US012642580B2

(12) United States Patent
Shadduck et al.

(10) Patent No.: US 12,642,580 B2
(45) Date of Patent: Jun. 2, 2026

(54) ELECTROSURGICAL DEVICES AND METHODS

(71) Applicant: Meditrina, Inc., San Jose, CA (US)

(72) Inventors: John H. Shadduck, Menlo Park, CA (US); Zsolt Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 1136 days.

(21) Appl. No.: 17/652,472

(22) Filed: Feb. 24, 2022

(65) Prior Publication Data

US 2022/0273358 A1 Sep. 1, 2022

Related U.S. Application Data

(60) Provisional application No. 63/154,518, filed on Feb. 26, 2021.

(51) Int. Cl.
*A61B 18/14* (2006.01)
*A61B 18/00* (2006.01)

(52) U.S. Cl.
CPC .................... *A61B 18/1447* (2013.01); *A61B 2018/00083* (2013.01); *A61B 2018/00577* (2013.01); *A61B 2018/00589* (2013.01); *A61B 2018/00642* (2013.01); *A61B 2018/1467* (2013.01); *A61B 2562/0214* (2013.01)

(58) Field of Classification Search
CPC ...... A61B 18/1447; A61B 2018/00083; A61B 2018/00577; A61B 2018/00589; A61B 2018/00642; A61B 2018/1467; A61B 2562/0214
See application file for complete search history.

(56) References Cited

U.S. PATENT DOCUMENTS

| | | | |
|---|---|---|---|
| 2005/0043728 A1* | 2/2005 | Ciarrocca | A61B 18/1482 606/50 |
| 2016/0106497 A1* | 4/2016 | Germain | A61B 18/1482 606/46 |
| 2020/0329953 A1 | 10/2020 | Truckai | |

* cited by examiner

*Primary Examiner* — Eun Hwa Kim
*Assistant Examiner* — Catherine Premraj
(74) *Attorney, Agent, or Firm* — Levine Bagade Han LLP

(57) ABSTRACT

A bipolar electrosurgical devices and methods of use for coagulation and ablation of tissue in a fluid-immersed working space is disclosed. The bipolar electrosurgical device can comprise a handle and an elongated shaft coupled to the handle. The bipolar electrosurgical device can further comprise a bipolar electrode arrangement and a return electrode. The bipolar electrode arrangement and the return electrode can be electrically insulated from one another. The bipolar electrosurgical device can further comprise an adjusting member carried by the elongated shaft. Movement of the adjusting member from a first position toward a second position can contemporaneously increase an effective surface area of the active electrode and decrease an effective surface area of the return electrode.

11 Claims, 9 Drawing Sheets

ELECTROSURGICAL DEVICES AND METHODS

CROSS-REFERENCE TO RELATED APPLICATIONS

This application claims benefit of priority to U.S. Provisional Patent Application No. 63/154,518 filed Feb. 26, 2021, the content of which is incorporated herein by reference in its entirety.

FIELD OF THE INVENTION

The present invention relates to bipolar electrosurgical devices and methods of use for coagulation and ablation of tissue in a fluid-immersed working space.

SUMMARY OF THE INVENTION

Some aspects in accordance with principles of the present disclosure relate to a bipolar electrosurgical device. The bipolar electrosurgical device can comprise a handle and an elongated shaft coupled to the handle. The bipolar electrosurgical device can further comprise a bipolar electrode arrangement and a return electrode. The bipolar electrode arrangement and the return electrode can be electrically insulated from one another. The bipolar electrosurgical device can further comprise an adjusting member carried by the elongated shaft. Movement of the adjusting member from a first position toward a second position can contemporaneously increase an effective surface area of the active electrode and decrease an effective surface area of the return electrode.

Movement of the adjusting member from the second position toward the first position can contemporaneously decrease the effective surface area of the active electrode and increase the effective surface area of the return electrode. In the first position, a ratio of the effective surface area of the active electrode to the effective surface area of the return electrode can be selected to provide a coagulation mode. In the first position, the effective surface area of the return electrode relative to the active electrode can be substantially greater than in the second position. In the second position, the effective surface area of the active electrode can be less than a surface area of the return electrode. In the second position, a ratio of the effective surface area of the active electrode to the effective surface area of the return electrode can be selected to provide a cut mode. In the first position, a ratio or the effective surface area of the active electrode to the effective surface area of the return electrode can be in a range of 0.5:1 to 1.5:1. In the second position, a ratio or the effective surface area of the active electrode to the effective surface area of the return electrode can be in a range of 1:5 to 1:50.

In another variation, a bipolar electrosurgical device. The bipolar electrosurgical device can comprise a handle and an elongated shaft coupled to the handle. The bipolar electrosurgical device can further comprise a bipolar electrode arrangement carried by a distal portion of the elongated shaft. The elongated shaft can further comprise an active electrode and a return electrode that are electrically insulated from one another. The bipolar electrode arrangement can further comprise a reciprocating mechanism configured to reciprocate the active electrode over a selected stroke at a selected rate to optimize plasma formation. The selected stroke can range from 1 mm to 10 mm. The selected rate ranges from 10 Hz to 1,000 Hz.

DETAILED DESCRIPTION

Figure 1:
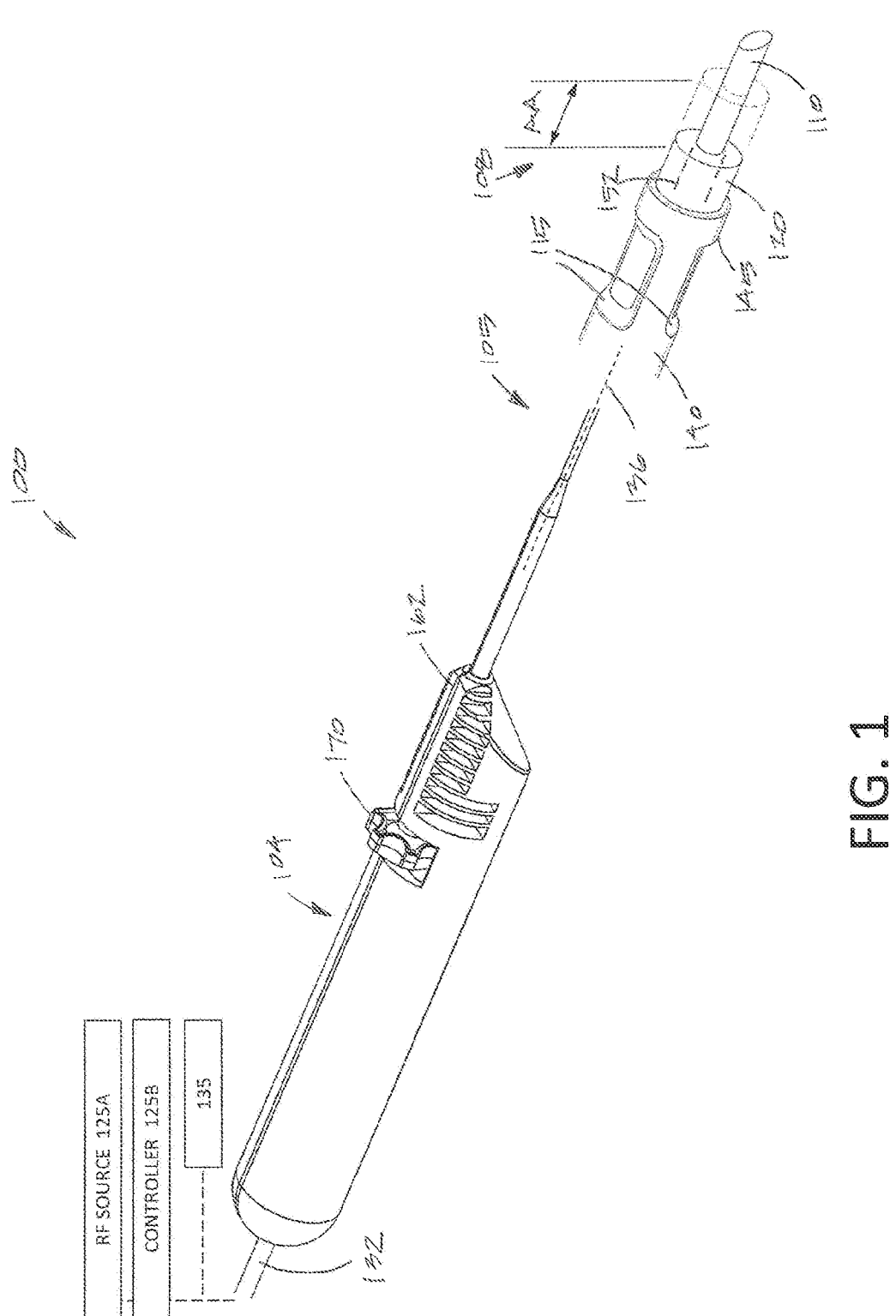
FIG. 1 is a perspective view of the RF device corresponding to the invention that has a handle connected to an elongate shaft with a working end carrying a bipolar electrode arrangement with a retractable-extendable dielectric member that is adapted to move and simultaneously adjust the surf are of the active electrode and the surface area and the return electrode.

FIG. 1 illustrates a bipolar RF tissue treatment device 100, which comprises a handle 104 coupled to a highly elongated shaft 105 having a diameter of 3 mm to 6 mm. The elongated shaft 105 of the RF device 100 is adapted for insertion through the working channel of an endoscope, as is known in the art. For example, the RF device 100 can be used with an endoscope of the type described in commonly-owned and co-pending U.S. Patent Application Publication No.

US2020/0329953 titled "ENDOSCOPE AND METHOD OF USE". The RF device 100 of FIG. 1 and its shaft 105 has a working end 108 that carries a bipolar electrode arrangement consisting of an active electrode 110 and the return electrode 115, as those terms are known in the art. The RF device 100 and its working end 108 are adapted to operate in a fluid-immersed working space in a patient's body, such as in a uterine cavity, where a conductive saline solution is used to distend the working space. While the RF device 100 is described herein for use in gynecologic procedures, the device may be used in urology and other procedures that utilize a fluid immersed working space. The cross-section of the elongated shaft 105 In FIG. 1 and the working end 108 is shown as being round, but other cross-sectional shapes are possible such as oval, polygonal, or other suitable shapes.

More in particular, the RF device 100 and working end 108 of the RF device shown in FIGS. 1-4B includes a mechanism for adjusting the bipolar electrode arrangement to thereby optimize the active and return electrodes 110, 115 for (i) a first coagulation mode of operation and (ii) a second cut or ablation mode of operation. The system for optimizing the bipolar electrode arrangement for the first and second modes of operation consists of an elongated, moveable adjusting member or dielectric member 120 in the elongated shaft 105 that can be manually moved to thereby simultaneously adjust the exposed surface areas of both the active electrode 110 and the return electrode 115. As is well known in the art, in a cut or ablation mode, the active electrode 110 in such a bipolar RF device requires that the surface area of the active electrode be very small relative to the surface area of the return electrode, which then concentrates the current flows, and energy density, in the small surface area of the active electrode 110. Such a small surface area of the active electrode causes the high energy density to create a vapor pocket or bubble in the saline environment around the active electrode 110, resulting in plasma formation or ignition in the vapor bubble. When such a vapor and resultant plasma are positioned in an interface with targeted tissue, the plasma will ablate, disintegrate, and molecularly disassociate the targeted tissue. In contrast, in the coagulation mode, it is known that the surface areas of the active electrode 110 and return electrode 115 should be somewhat similar in dimension to prevent high energy densities around the active electrode 110. It should be appreciated that the system of the invention is adapted to adjust the relative surface areas of the active electrode 110 and the return electrode 115 over a continuous range of surface area ratios to allow the physician to select any intermediate or combination coagulation/ablation mode of operation. In another variation, the RF device 100 and its RF source 125A and controller 125B can be adjusted to adjust the waveform between a coagulation waveform and an ablation waveform, or intermediate combination coagulation/cut waveforms as is known in the art as the movement of the dielectric member 120 adjust the electrode surface area between the coagulation mode and the ablation mode. Such an adjustment of the RF waveform can be responsive to a sensor 128 in the device handle 104 (FIG. 2) that senses the axial movement and location of the dielectric member 120 relative to the active and return electrodes 110, 115 as will be described further below.

Figure 2:
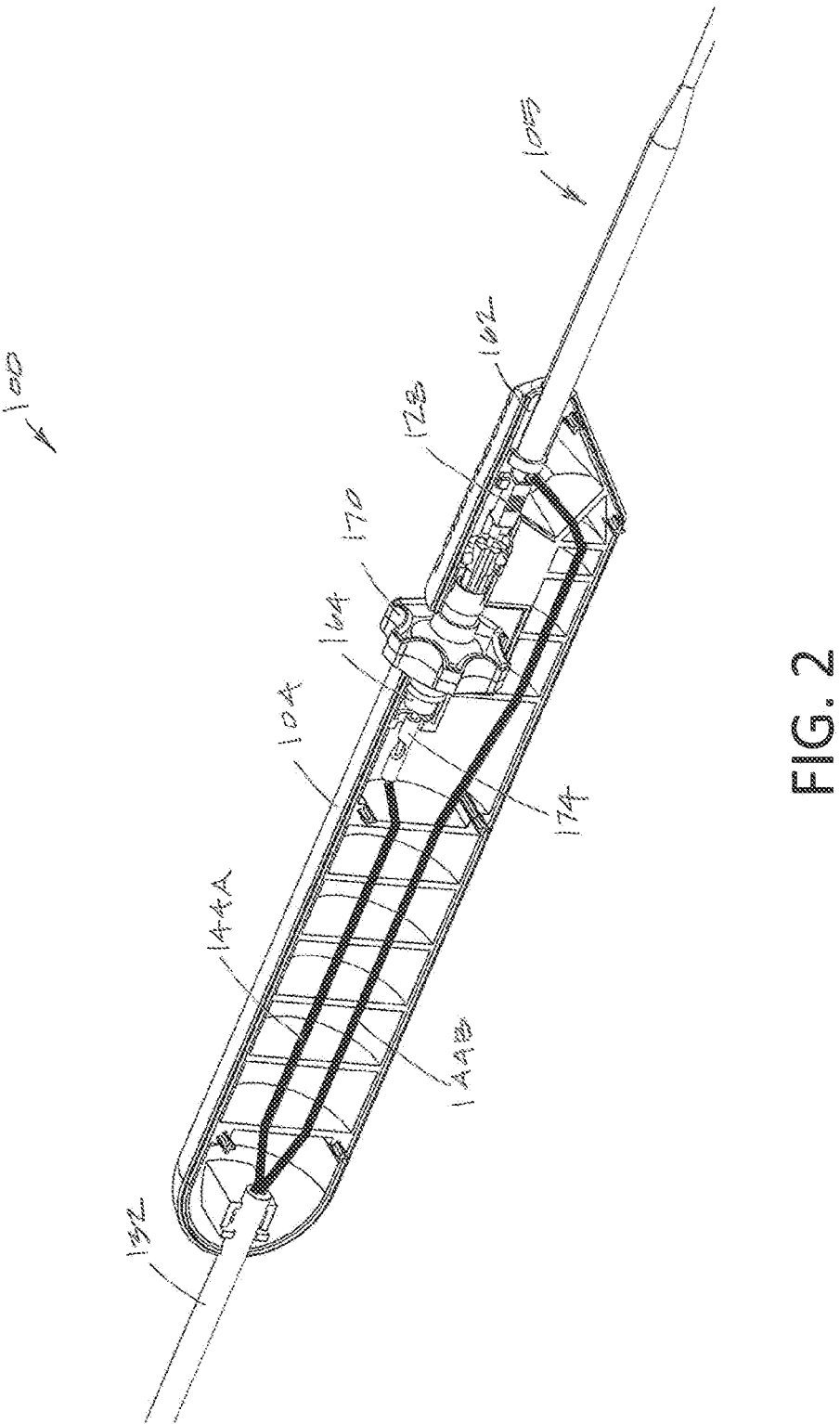
FIG. 2 is a perspective view of the handle of FIG. 1 with one side of the injection-molded handle removed to show the interior components of the handle.

Referring to FIGS. 1 and 2, the RF device 100 is coupled to the radiofrequency generator or RF source 125A and controller 125B through cable 132. In the variation shown in FIG. 1, a footswitch 135 can be used to activate the electrode arrangement to coagulate or cut tissue. In another variation, the electrosurgical components of the device can be actuated by one or more actuator buttons (not shown) in the handle 104.

Figure 3:
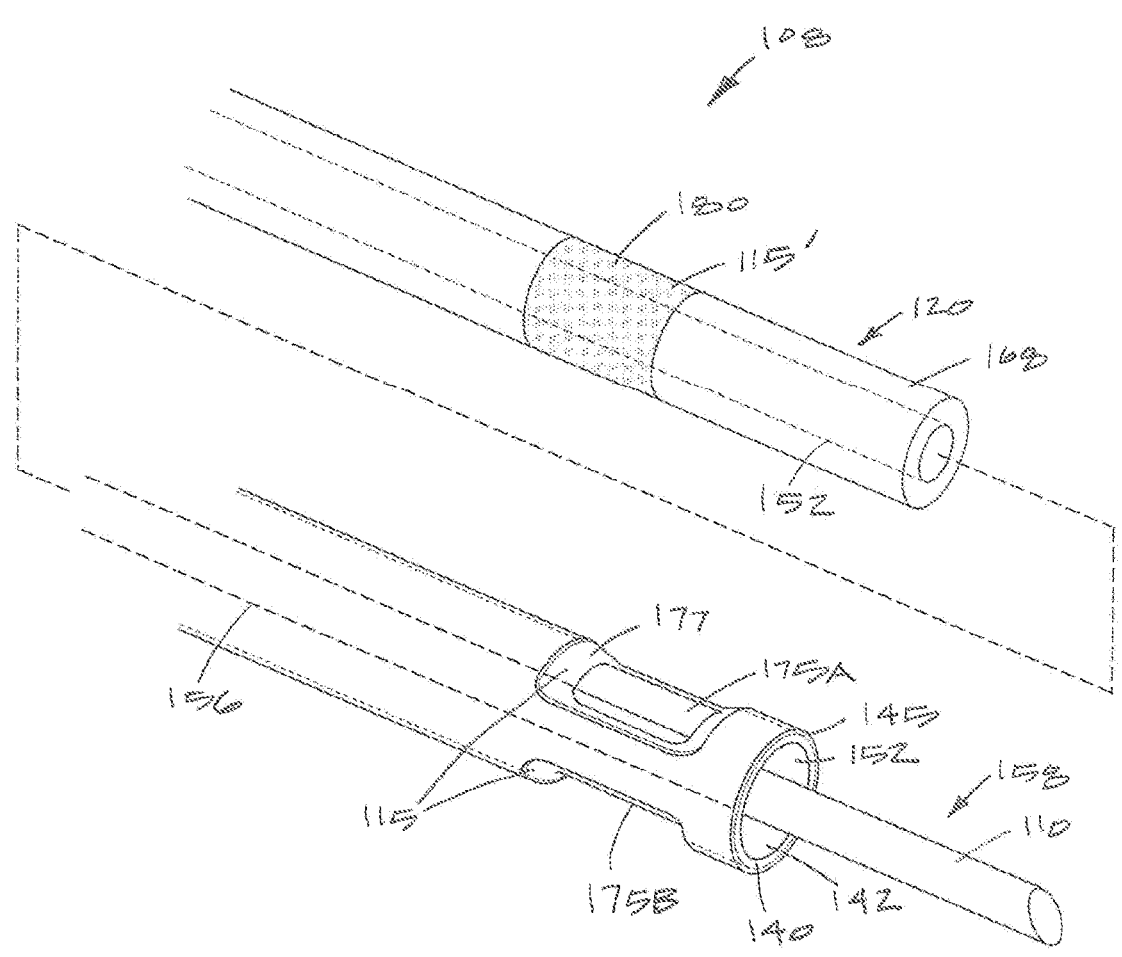
FIG. 3 is a perspective view of the working end of the RF device of FIG. 1 with an outer sleeve component comprising a return electrode and a central rod comprising an active electrode shown de-mated from a moveable dielectric member.

Referring to FIGS. 1, 2, and 3, the mechanisms for adjusting the relative surface areas of the active electrode 110 and return electrode 115 can now be described. In FIGS. 1 and 2, the elongate shaft 105 of the RF device 100 extends about longitudinal axis 136 and includes a thin wall, conductive outer sleeve 140 with passageway or bore 142 therein (FIG. 3). The elongated dielectric member 120 is axially movable (or rotationally movable in other variations) in the bore 142 of the outer sleeve 140, which is adapted to simultaneously reconfigure the surface areas of both the active and return electrodes 110, 115 between the coagulation mode configuration and the ablation mode configuration. In the variation of FIGS. 1-4B, the outer sleeve 140 is formed of a conductive metal such as stainless steel and is coupled to the RF source 125A by cable 132 and by first and second polarity leads 144A and 144B in the interior of the device handle 104 as shown in FIG. 2. Conductive lead 144B connects to the outer sleeve 140 in the interior of handle 104. The outer sleeve 140 is shown with a thin layer of an insulator 145 over the exterior of the sleeve 140, which can comprise any suitable thin heat shrink material such as a bio-compatible PFA, TEFLON®, polytetrafluoroethylene (PTFE), FEP (Fluorinated ethylene-propylene), polyethylene, polyamide, ECTFE (Ethylenechlorotrifluoro-ethylene), ETFE, PVDF, polyvinyl chloride or silicone.

Referring to FIGS. 1 and 3, the elongated dielectric member 120 has a central bore 152 therein and is axially slidable over an elongated, central conductive metal rod 156, which extends from the handle 104 through the elongated shaft 105 to an exposed distal end 158 that comprises the active electrode 110. As can be understood from FIG. 2, the outer sleeve 140 is fixed in its attachment to the handle 104, for example, by insert molding and/or adhesives at a distal end 162 of the handle 104. Similarly, the central metal rod 156 carrying active electrode 110 is maintained in a fixed relationship in the handle 104 by means of coupling 164 in the interior of the handle 104 (FIG. 2). Referring again to FIGS. 1 and 2, the handle 104 includes a finger-actuated actuator 170 that is adapted to move the dielectric member 120 distally and proximally relative to the fixed outer sleeve 140 and the fixed central metal rod 156. In FIG. 1, it can be seen that the distal end 168 of the dielectric member 120 is adapted to move back and forth over the active electrode 110, which may be a distance AA of 2 mm to 10 mm or more. In this variation, rotation of the actuator 170 uses a rotation-to-linear helical mechanism to move the dielectric member back and forth axially.

As will be described further below, the return electrode 115 comprises exposed portions of the wall 172 of the outer sleeve 140 (FIG. 3). Referring again to FIGS. 1 and 2, the RF device 100 is coupled to the radiofrequency generator or RF source 125 through cable 132. In FIG. 2, it can be seen that the first polarity lead 140A extends through the interior of the handle 104 to a connector 174 that connects the lead 140A to the central rod 156 and thereby to the active electrode 110 at the distal end 158 of the central rod 156. FIG. 2 further illustrates that a second polarity lead 140B extends from the cable 132 through the interior of the handle to electrically connect to the outer sleeve 140 and thereby to the return electrode 115 as described above.

Now turning to FIG. 3, the dielectric member 120 is shown de-mated from the outer sleeve 140 and the central conductive rod 156. In this variation, the outer sleeve 140 is configured with at least one opening or window in a distal region of the sleeve 140. This variation is shown with two windows, 175A and 175B, on opposing sides of the sleeve 140. It should be appreciated that the number of such windows or apertures in the outer sleeve 140 can number from 1 to 50 or more and the shapes of such windows as well as the configuration of the edges 177 of such windows 175A, 175B can have any suitable form to provide exposed surfaces which function as the return electrode 115. It can be understood that the return electrode's surface area RSA consists of at least the exposed edges 177 of windows 175A and 175B of the outer sleeve 140 that are not covered by the insulator layer 145.

FIG. 3 shows the de-mated, elongated dielectric member 120, which can comprise a ceramic or a combination of glass, polymer, and/or ceramic with the distal region 178 typically comprising a ceramic material. The distal region 178 of the dielectric member 120 carries an annular band 180 of a conductive material, such as stainless steel, that functions as a return electrode portion 115' when the surface area of the annular band 180 is exposed in a window 175A, 175B of the outer sleeve 140. Thus, it can be understood that the return electrode surface area RSA can comprise the surface area of the window edges 177 together with the exposed surface area of the annular band 180 within the windows 175A, 175B, which will vary depending on the axial position of the dielectric member 120. It can also be understood that the annular band 180 is electrically connected to the outer sleeve 140 and thus can function as a return electrode 115, since the outer surface of the annular band 180 is in slidable electrical contact with the non-insulated surface 182 of the bore 142 of the outer sleeve 140 to thus provide the conductive path to the return electrode 115.

Figure 4A:
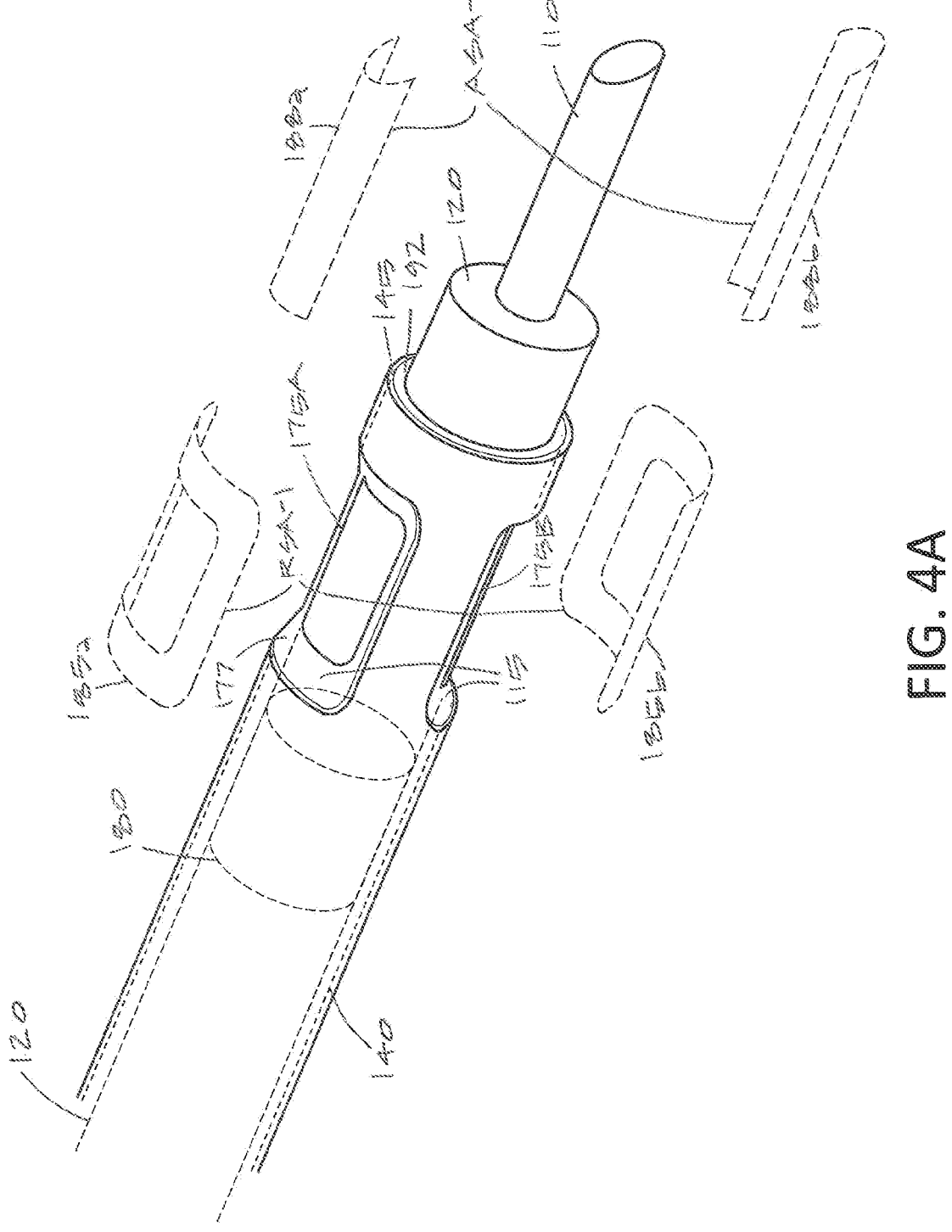
FIG. 4A is a perspective view of the working end of FIGS. 1 and 3 with the moveable dielectric member in a first retracted position which configures the active and return electrodes with similar surface areas to optimize the bipolar electrode arrangement for a coagulation mode of operation.
Figure 4B:
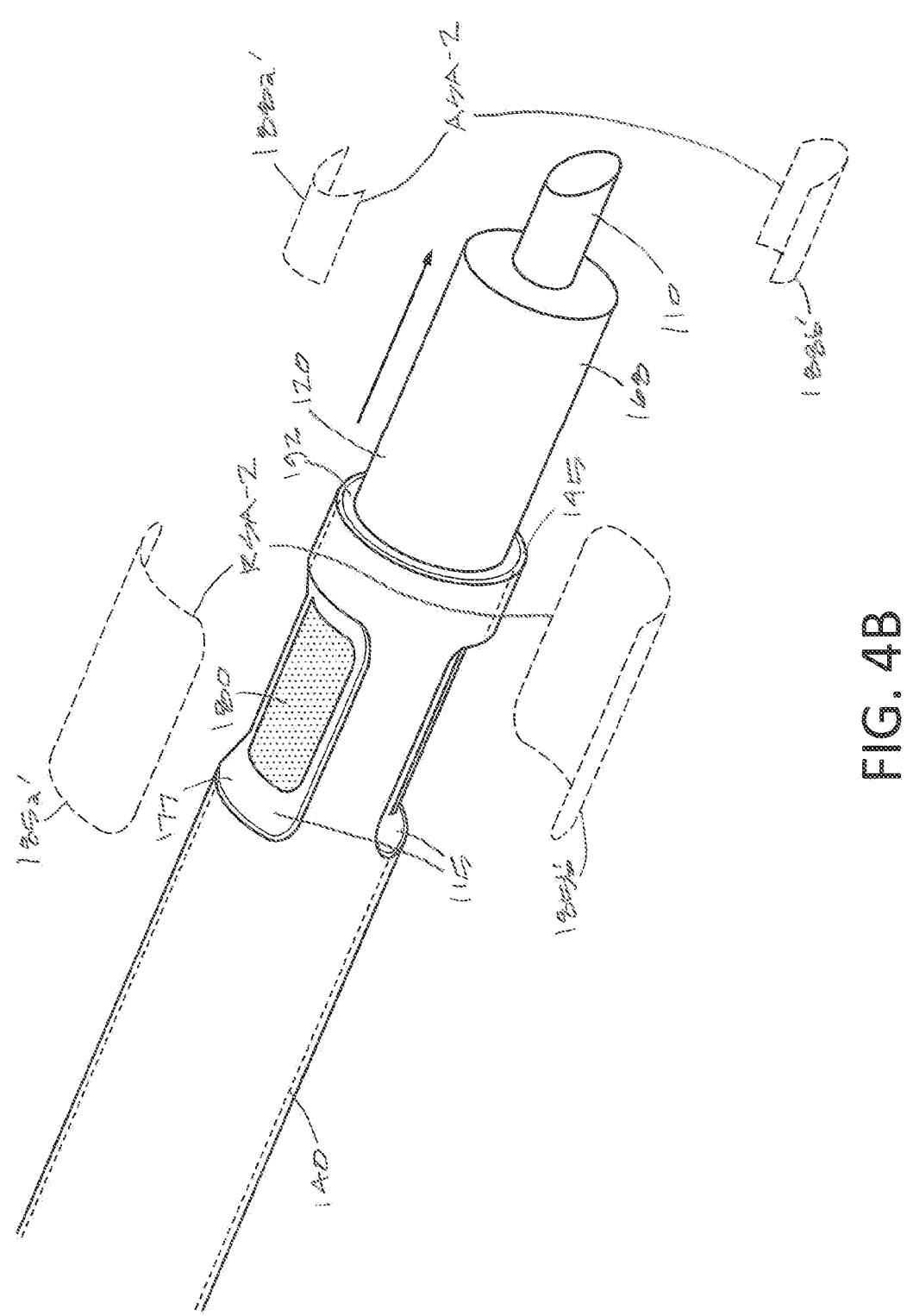
FIG. 4B illustrated the working end of FIG. 4A with the moveable dielectric member in a second extended position which configures the active and return electrodes with dissimilar surface areas to optimize the bipolar electrode arrangement for an ablation mode of operation.

Now turning to FIG. 4A-4B, it can be seen how axial movement of the dielectric member 120 is adapted to simultaneously adjust the return electrode surface area RSA and the active electrode surface area ASA to thereby optimize the electrode arrangement for either the tissue coagulation mode or the tissue ablation mode.

In FIG. 4A, it can be seen that the dielectric member 120 is a proximal or retracted position with the annular band 180 not exposed in windows 175A 175B of the outer sleeve 140. This axial position of dielectric member 120 in FIG. 4A provides an optimal configuration for the coagulation mode wherein the active and return electrodes 110 115 have similar exposed surface areas. In FIG. 4A, the return electrode surface area RSA-1 is illustrated as the area within dashed lines 185*a* and 185*b*, which outline the surfaces of (i) the superior-facing return electrode surface and (ii) the inferior-facing return electrode surfaces. Similarly, the dashed lines 188*a* and 188*b* outline the surface area of the (i) superior-facing active electrode surfaces and (ii) surface area of the inferior-facing return electrode surfaces. The return electrode also comprises the exposed distal end 192 of the outer sleeve 140. As can be seen in FIG. 4A, the total return electrode surface area RSA-1, and the total active electrode surface area ASA-1 are similar in dimension.

Now turning to FIG. 4B, the dielectric member 120 is moved to the extended or distal position wherein the annular band 180 of the dielectric member 120 is exposed in windows 175A and 175B of the outer sleeve 140. Thus, the return electrode surface area RSA-2 (within dashed lines 185*a*' and 185*b*') is enlarged since the window edges 177, the exposed distal end 192 of the outer sleeve wall, and the exposed surface of the annular band 180 function as return electrode 115'. At the same time, the active electrode surface area indicated at ASA-2 (within dashed lines 188*a*' and 188*b*') is significantly reduced by the extension of the distal portion 168 of the dielectric member 120 over the active electrode 110. Thus, in FIG. 4B, the relative surface areas RSA-2 and ASA-2 are optimized for the ablation mode. In this configuration, the active electrode 110 has a surface area ASA-2 that is far smaller than the surface area RSA-2 of the return electrode 115. This electrode arrangement results in very high energy densities around the active electrode 110, which instantly will create the vapor pocket or bubble and subsequent plasma formation around the active electrode 110 in a saline-immersed working space.

Figure 5:
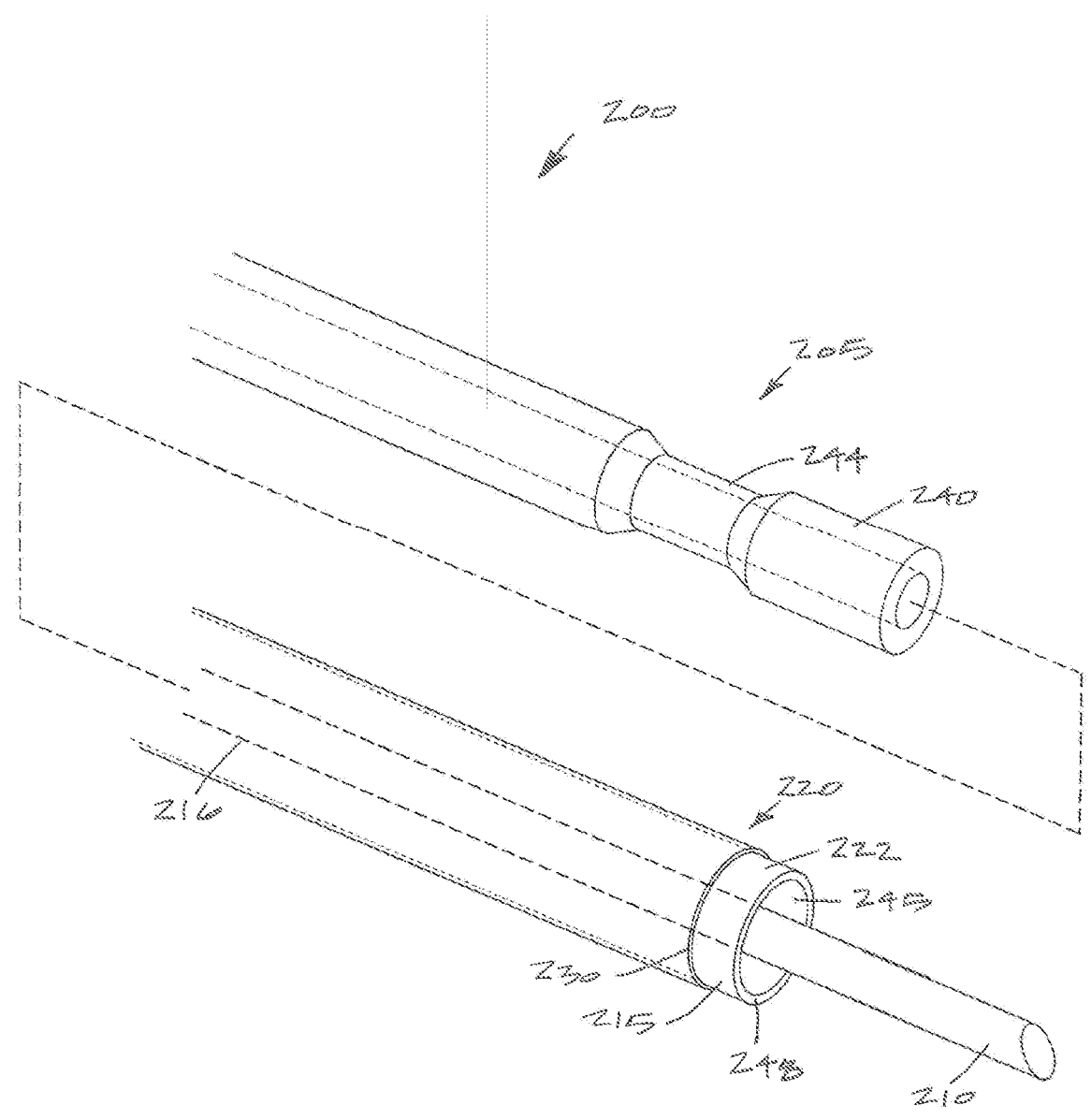
FIG. 5 is a perspective view of another variation of a working end of an RF device similar to that of FIG. 1 with a different form of a moveable dielectric member.
Figures 6A, 6B:
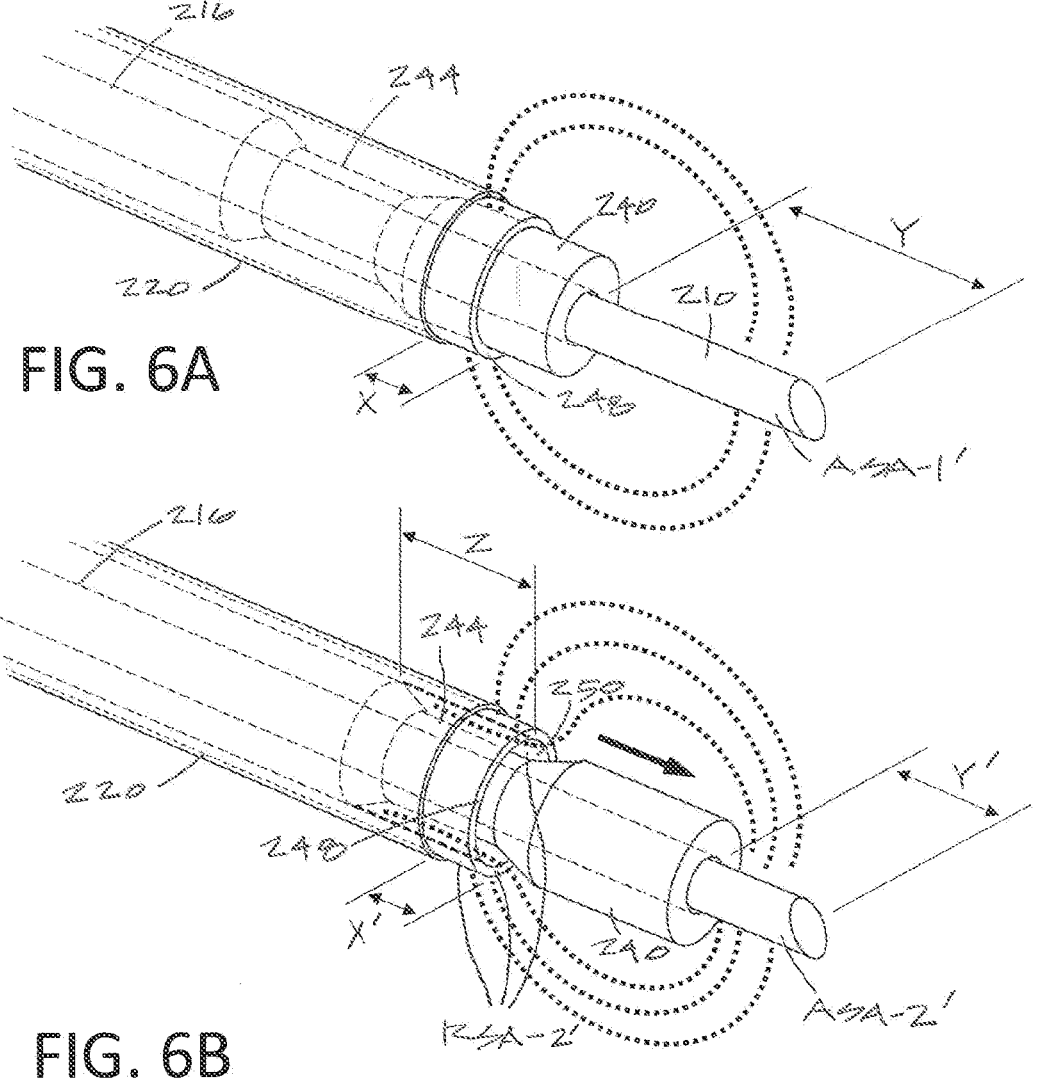
FIG. 6A is a perspective view of the working end of FIG. 5 with the moveable dielectric member in a first retracted position which configures the active and return electrodes with similar surface areas for a coagulation mode of operation.
FIG. 6B is a view of the working end of FIG. 5 with the moveable dielectric member in a second extended position which configures the active and return electrodes for an ablation mode of operation.

Now turning to FIGS. 5 and 6A-6B, another variation comprised an RF device 200 with a handle similar to that of FIG. 1 with a working end 205 shown in FIG. 5, which functions similar to the RF device 100 of FIGS. 1-4B. In the working end variation 205 shown in FIG. 5 with the components de-mated, it can be seen that an active electrode 210 and return electrode 215 are in an arrangement similar to the previous variation. In FIG. 5, a central conductive rod 216 is fixed in the handle (not shown) as described previously, where the active electrode 210 comprises the distal end 218 of the conductive rod 216. In FIG. 5, the outer sleeve 220 again comprises a thin-wall conductive material, where the distal end 222 comprises the return electrode 215. In this variation, the outer sleeve 220 again carries an outer insulator layer 230, except that a distal portion 222 of the outer sleeve 220 is exposed to comprise the return electrode 215. The outer sleeve 220 is fixed in handle (cf. FIG. 2) as described in the previous variation in that it is maintained in a fixed relationship with the central conductive rod 216.

In FIG. 5, it can be seen that the dielectric adjusting member 240 does not carry a conductive annular band 180 as in the previous variation of FIG. 3. The working end 205 of FIG. 5 shows that the dielectric member 240 is configured with an annular notch or recess 244, which is further described below. The dielectric member is adapted to move axially in bore 245 of the outer sleeve 220. Now turning to FIGS. 6A and 6B, it can be seen that extension and retraction of the dielectric member 240 can simultaneously adjust the surface areas of the active electrode 210 and return electrode 215 to optimize the electrode arrangements for tissue coagulation and tissue ablation as described previously.

In FIG. 6A, the dielectric member 240 is shown in a retracted position and the return electrode 215 has a surface area RSA-1' that comprises the exposed circumferential surface of the distal portion 222 of the outer sleeve 220, which extends over an axial length X together with the surface area of the distal sleeve edge 248. In FIG. 6A, the active electrode surface area ASA-1' comprises the circumferential surface of the exposed rod 216 having an axial length Y. In this position of the dielectric member 240, it can be seen that the surface area ASA-1' of the active electrode is equal to or larger than the surface area RSA-1' of the return electrode, which is optimal for tissue coagulation with the active electrode 210. The RF current paths are indicated at CP between the active and return electrodes 210 and 215.

In FIG. 6B, the working end 205 is shown with the dielectric member 240 moved to the distal or extended position after having been actuated by the actuator in the handle as described in the previous variation. In FIG. 6B, it can be seen that the active electrode surface area surface ASA-2' is greatly reduced and comprises the surface of the rod 216 extending over the limited axial length indicated at Y'. FIG. 6B further shows that the surface area RSA-2' of the return electrode is greatly increased wherein such a return electrode surface area RSA-2' now consists of the circumferential outer surface of distal portion 222 of outer sleeve 220, surface area of sleeve edge 248, and the inner circumferential surface 250 of the bore 245 in the outer sleeve 220 having length Z which is now exposed due to the annular recess 244 in the dielectric member 240 which allows conductive saline fluid to flow into the open bore 245 of the outer sleeve 220. Thus, it can be understood from FIG. 6B that the surface area ASA-2' of the active electrode 210 is small relative to the total surface area RSA-2' of the return electrode 215, which thus optimizes the electrode arrangement for the ablation mode. In FIG. 6B, the RF current paths CP' are shown between the active electrode 210 and the various surfaces 222, 248, and 250 of the outer sleeve 220 comprising the return electrode 215.

In general, a bipolar electrosurgical device corresponding to the invention comprises a handle coupled to an elongated shaft, a bipolar electrode arrangement carried by a distal portion of the elongated shaft with an active electrode and a return electrode that are electrically insulated from one another by a dielectric adjusting member within the elongated shaft, wherein movement of the dielectric member from a first position toward a second position contemporaneously increases the effective surface area of the active electrode and decreases the effective surface area of the return electrode. Further, movement of the dielectric member from the second position toward the first position contemporaneously decreases the effective surface area of the active electrode and increases the effective surface area of the return electrode. In the first position, the ratio or the effective surface area of the active electrode to the effective surface area of the return electrode is in the range of 0.5:1 to 1.5:1. In the second position, the ratio of the effective surface area of the active electrode to the effective surface area of the return electrode is in the range of 1:5 to 1:50.

Figure 7:
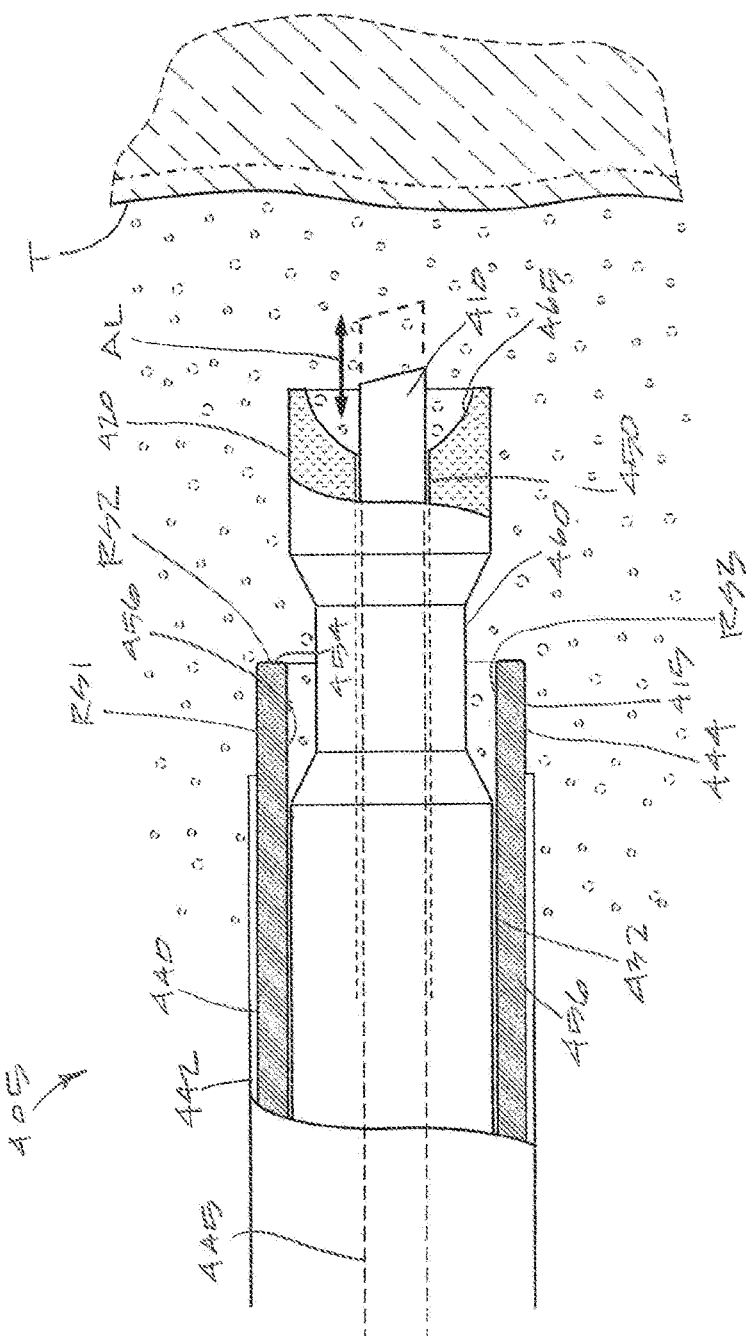
FIG. 7 is a cut-away view of another variation of a working end of an RF device similar to that of FIGS. 5, 6A, and 6B, which includes a mechanism for reciprocating the active electrode when operating in the ablation mode.
Figures 8A, 8B:
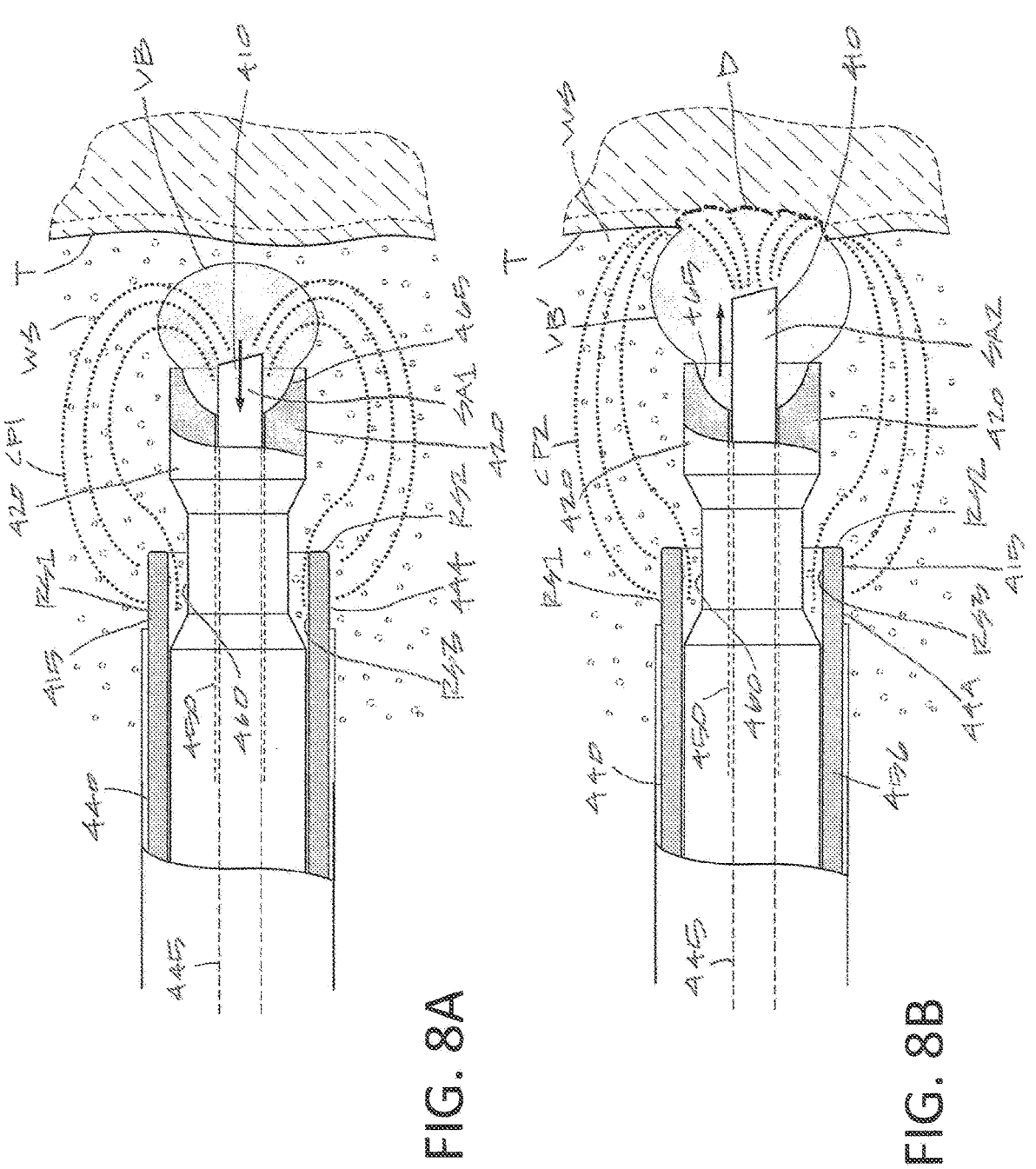
FIG. 8A illustrates the working end of FIG. 7 with the reciprocating active electrode in a proximal position which concentrated RF energy density about the active electrode to enhance formation of a vapor bubble and subsequent plasma in a saline-immersed working space.
FIG. 8B illustrates the working end of FIG. 8A with the reciprocating active electrode at a distal end of its stroke, which increases the surface area of the active electrode to enhance ablation of tissue with plasma formed in the vapor bubble.

Now turning to FIGS. 7 and 8A-8B, another variation of an RF device is similar to that of FIG. 1, with FIG. 7 showing a cut-away view of its working end 405. The bipolar electrode arrangement of the working end 405 of FIG. 7 has an active electrode 410 and return electrode 415 that are somewhat similar to working end 205 of FIGS. 5-6B. In the variation shown in FIG. 7, the dielectric member 420 again is movable from a retracted, proximal position (not shown; cf. FIG. 6A) to an extended, distal position shown in FIG. 7. The axial movement of the dielectric member 420 functions as in the previous variation to change the surface areas of the active electrode 410 and the return electrode 415 to optimize the electrode arrangement for either (i) coagulation mode or (ii) ablation mode or any intermediate combination coagulation/ablation mode. The dielectric member 420, as in previous variations, is axially moveable in bore 432 of the outer sleeve 440. The outer sleeve 440 has an outer insulator layer 442 except for the distal end 444 of the sleeve 440, which comprises the return electrode 415. However, in the variation of FIGS. 7 and 8A-8B, the RF device 400 incorporates additional functionality that performs an ablation-enhancing function which is actuated only when the dielectric member 420 is moved toward or to its extended, distal position as depicted in FIG. 7.

As can be seen in FIG. 7, the RF device's working end 405 has an elongated central rod 445 with a distal end 448 that comprises the active electrode 410. In this variation, the central rod 445 and active electrode 410 are adapted to be reciprocated at high speed in a bore 450 in the dielectric adjusting member 420. In FIG. 7, it can be seen that the central rod 445 can be reciprocated at high speed over a stroke having an axial length ΔL that can range from 1 mm to 10 mm at reciprocation rates that can range from 10 Hz to 1,000 Hz. The reciprocation is provided by a motor in a handle of the device (not shown). As can be seen in FIG. 7, the return electrode 415 comprises the sum of the (i) the surface area RS1 of the circumferential outer surface of the distal end 444 of the outer sleeve 440; (ii) the surface area RS2 of the distal edge 454 of outer sleeve 440; and (iii) the surface area RS3 of the circumference of the inner surface 456 of the wall of outer sleeve 440 which provides a large return electrode surface area. In FIG. 7, it can be seen that the dielectric sleeve 420 has an annular recess 460 that allows for exposure of the inner surface 456 of the outer sleeve 440 to allow it to function as a return electrode 415. In the variation of working end 405 shown in FIG. 7, the dielectric member 420 has a distal concavity or recess 465 that is adapted to enhance the formation of a vapor pocket and subsequent high-energy plasma for ablation or cutting of targeted tissue T as is known in the art.

Now referring to FIGS. 8A and 8B, it can be how the high-speed reciprocation of the active electrode 410 can enhance the speed of tissue cutting or ablation. In FIG. 8A, the active electrode 410 is at a proximal position of its stroke and is energized by turning on RF current flow between the active and return electrodes 410 and 415. The RF current paths CP1 are shown schematically where the reduced surface area SA1 of the active electrode 410 creates high energy densities about the electrode 410 to thereby instantly create a vapor bubble VB and plasma therein within the recess 465 of the dielectric member and about the electrode 410. As the vapor bubble VB expands in microseconds or milliseconds, shown in FIG. 8B, it is advantageous to have an increased surface area SA2 of the active electrode 410 to cause RF current paths CP2 to extend through the targeted tissue T in contact with the vapor bubble VB and plasma to thereby cause the tissue ablation or disintegration indicated at D in FIG. 8B. By this means of high-speed reciprocation of the active electrode 410, the continuous, practically instantaneous expansion and collapse of the vapor bubble VB and plasma ignition therein in an interface with targeted tissue T will enhance the speed of tissue ablation for any selected RF power setting. The speed of reciprocation of the active electrode 410 can be selected to optimize vapor bubble formation and collapse, which has been found to be in the range of 10 Hz to 1,000 Hz and more often in the range of 500 Hz to 1,000 Hz.

Although particular variations of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

We claim:

1. A bipolar electrosurgical device, comprising:
   a handle;
   an elongated shaft coupled to the handle, the elongated shaft comprising an outer sleeve having one or more windows;

a bipolar electrode arrangement carried by a distal portion of the elongated shaft comprising an active electrode and a return electrode that are electrically insulated from one another; and an adjusting member carried by the elongated shaft, wherein movement of the adjusting member with respect to the outer sleeve from a first position toward a second position contemporaneously increases an effective surface area of the active electrode and decreases an effective surface area of the return electrode by positioning the return electrode retracted from being exposed in the one or more windows.

2. The bipolar electrosurgical device of claim 1, wherein movement of the adjusting member from the second position toward the first position contemporaneously decreases the effective surface area of the active electrode and increases the effective surface area of the return electrode.

3. The bipolar electrosurgical device of claim 2, wherein in the first position, a ratio of the effective surface area of the active electrode to the effective surface area of the return electrode is selected to provide a coagulation mode.

4. The bipolar electrosurgical device of claim 2, wherein in the first position, the effective surface area of the return electrode relative to the active electrode is substantially greater than in the second position.

5. The bipolar electrosurgical device of claim 2, wherein in the second position, the effective surface area of the active electrode is less than the effective surface area of the return electrode.

6. The bipolar electrosurgical device of claim 2, wherein in the second position, a ratio of the effective surface area of the active electrode to the effective surface area of the return electrode is selected to provide a cut mode.

7. The bipolar electrosurgical device of claim 2, wherein in the first position, a ratio of the effective surface area of the active electrode to the effective surface area of the return electrode is in a range of 0.5:1 to 1.5:1.

8. The bipolar electrosurgical device of claim 4, wherein in the second position, a ratio of the effective surface area of the active electrode to the effective surface area of the return electrode is in a range of 1:5 to 1:50.

9. A bipolar electrosurgical device, comprising:

a handle;

an elongated shaft coupled to the handle, the elongated shaft comprising an outer sleeve having a bore;

a dielectric member axially moveable in the bore, wherein the dielectric member comprises an annular recess that exposes an inner surface of the outer sleeve;

a bipolar electrode arrangement carried by a distal portion of the elongated shaft comprising an active electrode and a return electrode that are electrically insulated from one another, wherein a surface area of the active electrode and a surface area of the return electrode change upon axial movement of the dielectric member, wherein the return electrode is located at the inner surface of the outer sleeve; and a reciprocating mechanism configured to reciprocate the active electrode over a selected stroke at a selected rate to optimize plasma formation.

10. The bipolar electrosurgical device of claim 9, wherein the selected stroke ranges from 1 mm to 10 mm.

11. The bipolar electrosurgical device of claim 9, wherein the selected rate ranges from 10 Hz to 1,000 Hz.

* * * * *